United States Patent
Yeo

(10) Patent No.: US 11,132,361 B2
(45) Date of Patent: Sep. 28, 2021

(54) SYSTEM FOR RESPONDING TO COMPLEX USER INPUT QUERIES USING A NATURAL LANGUAGE INTERFACE TO DATABASE

(71) Applicant: INTERNATIONAL BUSINESS MACHINES CORPORATION, Armonk, NY (US)

(72) Inventor: Hangu Yeo, Westchester, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 247 days.

(21) Appl. No.: 16/196,475

(22) Filed: Nov. 20, 2018

(65) Prior Publication Data

US 2020/0159848 A1 May 21, 2020

(51) Int. Cl.
*G06N 20/00* (2019.01)
*G06F 16/2455* (2019.01)
*G06F 16/242* (2019.01)
*G16H 10/60* (2018.01)
*G06F 16/28* (2019.01)

(52) U.S. Cl.
CPC ........ *G06F 16/243* (2019.01); *G06F 16/2455* (2019.01); *G06F 16/288* (2019.01); *G06N 20/00* (2019.01); *G16H 10/60* (2018.01)

(58) Field of Classification Search
CPC .. G06F 16/3329; G06F 16/243; G06F 16/288; G06N 20/00; G16H 10/60
USPC ........................................................ 707/771
See application file for complete search history.

(56) References Cited

U.S. PATENT DOCUMENTS

| 9,575,963 | B2 | 2/2017 | Pasupalak et al. |
| 9,792,347 | B2 | 10/2017 | Guo et al. |
| 9,971,766 | B2 | 5/2018 | Pasupalak et al. |
| 2006/0184393 | A1* | 8/2006 | Ewin ...................... G06Q 50/22 705/2 |
| 2008/0294507 | A1* | 11/2008 | Reiner .................. G06F 19/321 705/2 |
| 2014/0279837 | A1 | 9/2014 | Guo et al. |

(Continued)

OTHER PUBLICATIONS

Silvia Quarteroni and Suresh Manandhar, "Adaptivity in Question Answering with User Modeling and a Dialog Interface," Proceedings of the Eleventh Conference of the European Chapter of the Association for Computational Linguistics (EACL), pp. 199-202, 2006.

(Continued)

*Primary Examiner* — Robert W Beausoliel, Jr.
*Assistant Examiner* — Pedro J Santos

(57) ABSTRACT

A system for responding to natural language medical queries is provided. The system includes a memory storing a computer program and a processor configured to execute the computer program. The computer program decomposes an input medical related user query into medical related sub-queries using pre-defined proxies, rephrases the sub-queries into yes-no queries answerable with a yes or a no, extracts feature values from the yes-no queries and a relational database storing clinical records, generates a feature vector from the extracted feature values, and applies the feature vector along with desired output labels to a supervised machine learning algorithm to generate a classifier configured to answer a new medical related user query.

20 Claims, 8 Drawing Sheets

(56) References Cited

U.S. PATENT DOCUMENTS

| | | | | |
|---|---|---|---|---|
| 2014/0350961 | A1* | 11/2014 | Csurka | G16H 10/60 |
| | | | | 705/3 |
| 2016/0124954 | A1 | 5/2016 | Bishop et al. | |
| 2020/0219617 | A1* | 7/2020 | Eleftheriou | G16H 10/20 |

OTHER PUBLICATIONS

Fei Li and H.V. Jagadish, "Constructing an Interactive Natural Language Interface for Relational Databases," Proceedings of the VLDB Endowment, vol. 8, pp. 73-84, 2014.

Omar Al-Harbi, Shaidah Jusoh and Norita Norwawi, "Handling Ambiguity Problems of Natural Language Interface for Question Answering," International Journal of Computer Science Issues, vol. 9, No. 3, May 2012, pp. 17-25.

Sven Hartrumpf, "Semantic Decomposition for Question Answering," Proceedings of the 18th European Conference on Artificial Intelligence (ECAI), pp. 313-317, 2008, Patras, Greece.

Finley Lacatusu, Andrew Hickl and Sanda Harabagiu, "Impact of Question Decomposition on the Quality of Answer Summaries," Proceedings of Language Resources and Evaluation Conference (LREC), 2006, pp. 1147-1152.

Boris Katz, Gary Borchardt and Sue Felshin, "Syntactic and Semantic Decomposition Strategies for Question Answering from Multiple Resources," Proceedings of the AAAI 2005 Workshop on Inference for Textual Question Answering, pp. 35-41, 2005.

John Prager, Jennifer Chu-Carroll and Krzysztof Czuba, "Question Answering using Constraint Satisfaction: QA-by-Dossierwith-Constraints," Proceedings of the 42nd Annual Meeting on Association for Computational Linguistics, Jul. 2004.

Hannaneh Hajishirzi and Erik T. Mueller, "Question Answering in Natural Language Narratives Using Symbolic Probabilistic Reasoning," Proceedings of the 25th International Florida Artificial Intelligence Research Society Conference, 2012, pp. 38-43.

Kirk Roberts, Halil Kilicoglu, Marcelo Fiszman, and Dina Demner-Fushman, "Decomposing Consumer Health Questions," Proceedings of the 2014 Workshop on Biomedical Natural Language Processing (BioNLP 2014), Jun. 2014, pp. 29-37.

Adam Lally, Sugato Bachi, Michael A. Barborak, David W. Buchanan, Jennifer Chu-Carroll, David A. Ferrucci, Michael R. Glass, Aditya Kalyanpur, Erik T. Mueller, J. William Murdock, Siddharth Patwardhan, John M. Prager and Christopher A. Welty, "WatsonPaths: Scenario-based Question Answering and Inference over Unstructured Information," IBM Research Report, RC25489, IBM T. J. Watson Research Center, Sep. 2014.

I. Androutsopoulos, G.D. Ritchie and P. Thanisch, "Natural Language Interfaces to Databases—An Introduction," Journal of Natural Language Engineering, 1994, 1-49.

* cited by examiner

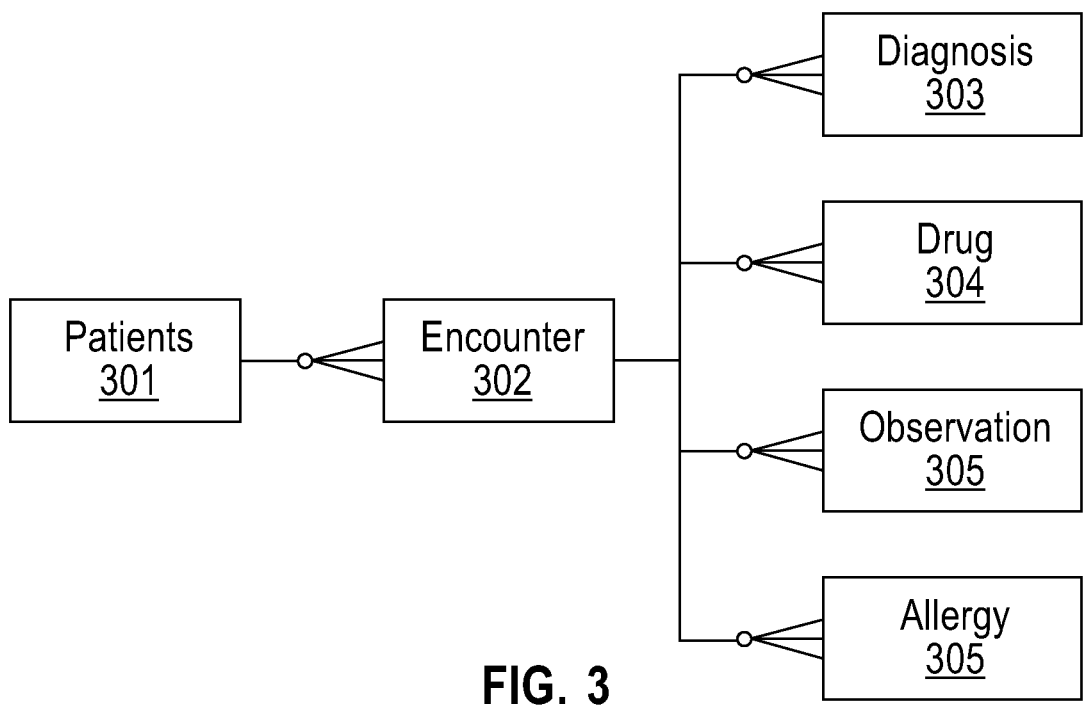

FIG. 3

1. Answer "Cured"

If there are no follow up encounters in the next {certain number of days}.

2. Answer "Not Cured"

If another diagnosis with {the same disease} within {a certain number of days}.
   If another {the same medication treatment} within {a certain number of days}.
   If {subsequent encounter} within {a certain number of days}.

3. Answer "Adverse Event"

If allergic reaction to {a certain medication treatment} within {a certain number of days}.
   If {a certain side effect A} associated with {a certain medication treatment}.
   ....
   If {a certain side effect N} associated with {a certain medication treatment}.

FIG. 4

SYSTEM FOR RESPONDING TO COMPLEX USER INPUT QUERIES USING A NATURAL LANGUAGE INTERFACE TO DATABASE

BACKGROUND

1. Technical Field

The present disclosure relates generally to a system for responding to complex user input queries, and more particularly to a system for responding to natural language medical queries using a natural language to interface database.

2. Discussion of Related Art

Big Data is generating huge interests and has made changes in every industry and one of the most promising areas it can be applied to is healthcare. It is common that healthcare data sets include several years of hospital admission, clinical and treatment records that allow doctors or researchers to see relevant patterns in admission rates or treatment results. In order to help users to use large amounts of data to find trends and treatments that have the highest rates of success, patient databases from different institutions or hospitals are linked together.

There has been a challenge of getting various forms of data (for example, structured, semi-structured and unstructured) into the conventional relational database, and efforts have been made for transition from relational databases to big data happening in the real world.

Structured Query Language (SQL) is a standard query language to retrieve information stored in relational database, and common Relational Database Management Systems (RDBMS) use SQL and have their own proprietary extensions. Hence, users need to learn the query language and be familiar with the database management system and database schema to formulate the query to produce the desired output query results.

However, the end users who interact with the structured database do not always have a technical background and often are intimidated to write a code in a query language, and it is often challenging for non-technical end users to query relational databases without being trained technically.

People use natural language to communicate and ask questions in the real world. The Natural Language Interface to Database (NLIDB) is an application that relies on a Natural Language Processing (NLP) technique and has been developed to help users to query databases using natural languages such as English.

BRIEF SUMMARY

According to an exemplary embodiment of the inventive concept, a system for responding to natural language medical queries is provided. The system includes a memory storing a computer program and a processor configured to execute the computer program. The computer program decomposes an input medical related user query into medical related sub-queries using pre-defined proxies, rephrases the sub-queries into yes-no queries answerable with a yes or a no, extracts feature values from the yes-no queries and a relational database storing clinical records, generates a feature vector from the extracted feature values, and applies the feature vector along with desired output labels to a supervised machine learning algorithm to generate a classifier configured to answer a new medical related user query.

According to an exemplary embodiment of the inventive concept, a method for responding to natural language medical queries is provided. The method includes: decomposing an input medical related user query into medical related sub-queries using pre-defined proxies; rephrasing the sub-queries into yes-no queries answerable with a yes or a no; extracting feature values from the yes-no queries and a relational database storing clinical records; generating a feature vector from the extracted feature values; applying the feature vector along with desired output labels to a supervised machine learning algorithm to generate a classifier; and applying a new medical related user query to the classifier.

According to an exemplary embodiment of the inventive concept, a computer program product for responding to natural language medical queries is provided. The computer program product includes a computer readable storage medium having program code embodied therewith. The program code is executable by a processor, to perform method steps including instructions for: decomposing an input medical related user query into medical related sub-queries using pre-defined proxies; rephrasing the sub-queries into yes-no queries answerable with a yes or a no; extracting feature values from the yes-no queries and a relational database storing clinical records; generating a feature vector from the extracted feature values; applying the feature vector along with desired output labels to a supervised machine learning algorithm to generate a classifier; and applying a new medical related user query to the classifier.

BRIEF DESCRIPTION OF THE SEVERAL VIEWS OF THE DRAWINGS

Exemplary embodiments of the invention can be understood in more detail from the following descriptions taken in conjunction with the accompanying drawings in which:

FIG. 3 illustrates an exemplary healthcare data model;

FIG. 4 illustrates exemplary proxies created by a healthcare expert;

DETAILED DESCRIPTION OF THE EXEMPLARY EMBODIMENTS

Figure 1:
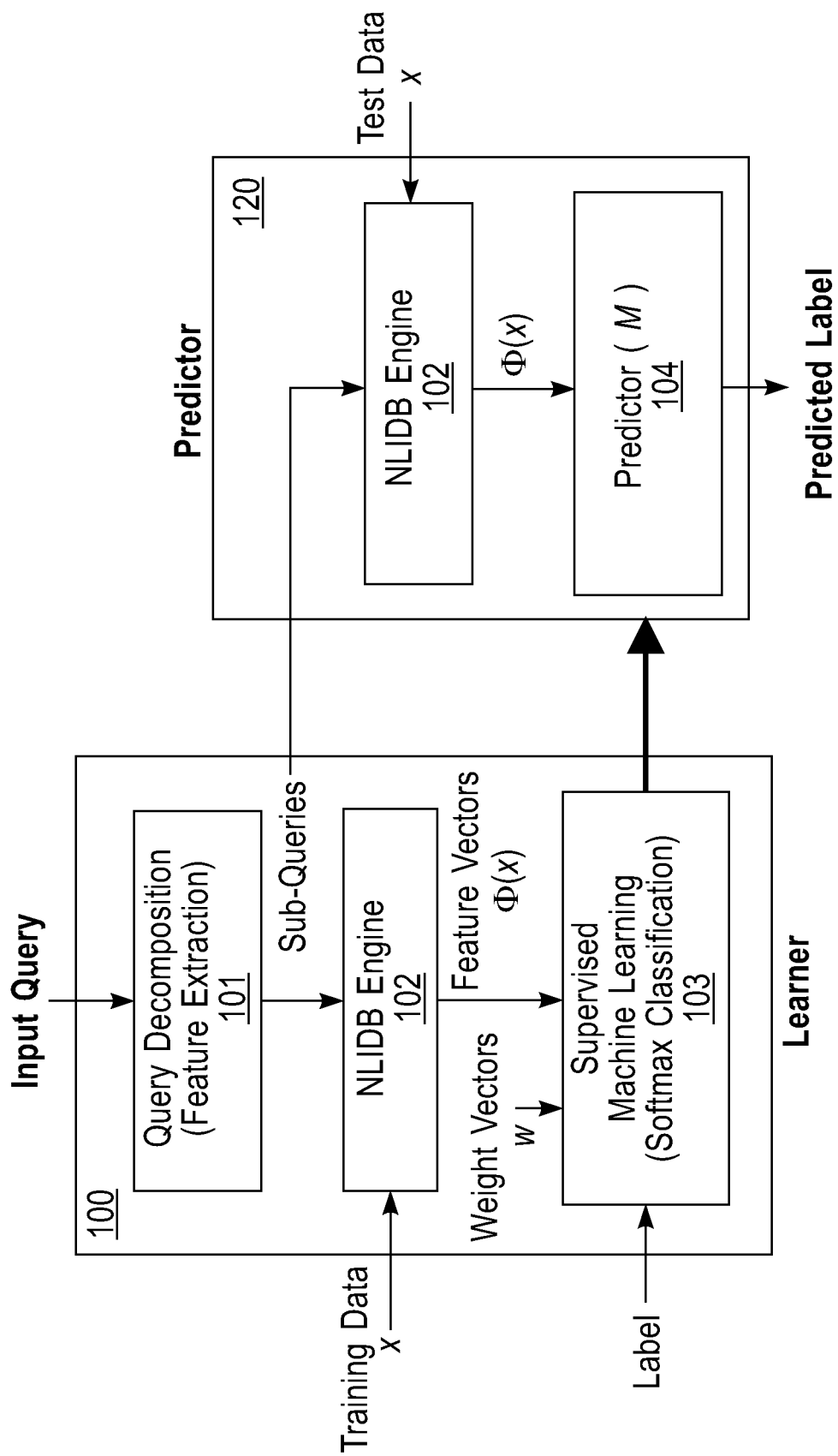
FIG. 1 illustrates a system for responding to natural language queries according to an exemplary embodiment of the inventive concept.

The inventive concept will be described in more detail with reference to the accompanying drawings, where exemplary embodiments of the present disclosure have been illustrated. Throughout the drawings, same or like reference numerals are used to represent the same or like components.

However, the present inventive concept can be implemented in various manners, and thus should not be construed to be limited to the embodiments disclosed herein. On the contrary, those embodiments are provided for the thorough and complete understanding of the present disclosure to convey the scope of the present disclosure to those skilled in the art.

Figure 2:
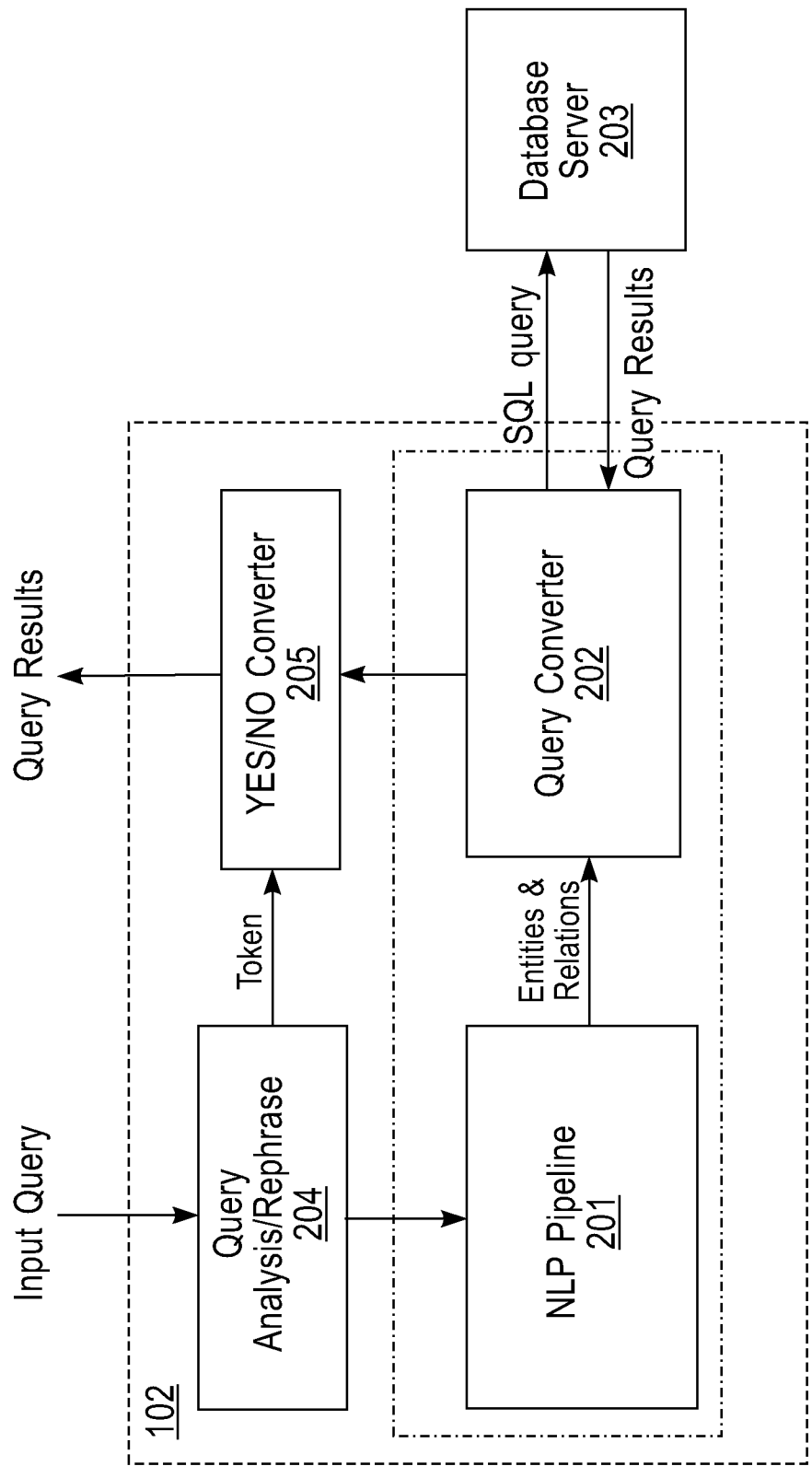
FIG. 2 illustrates an embodiment of a natural language interface to database (NLIDB) engine illustrated in FIG. 1.

FIG. 1 illustrates a system for responding to natural language medical queries according to an exemplary embodiment of the inventive concept. FIG. 2 illustrates an embodiment of natural language interface to database (NLIDB) engine illustrated in FIG. 1. The system is based on supervised machine learning that infers a classifier (or a predictor 104) from supervised training clinical data. Unlike a rule-based expert system, the present system is based on statistical modeling of data. The training data consists of a set of training samples where each training sample consists of an input vector and output label.

The system may use Weight Vectors w to classify the input records into output labels. Each weight vector comprises parameters that model the problem and specifies the contribution of each feature to classify the input records into output labels.

A Query Decomposition unit 101 of the System decomposes a user query (e.g., an input query) into sub-queries. A natural language interface to database engine (NLIDB) 102 of the system uses the sub-queries to extract feature values from clinical records stored in a database 203 (e.g., a relational database). The extracted feature values are used to constitute an input vector. For example, each decomposed sub-query is treated as a feature, and the answers to the sub-queries constitute a feature vector, and the feature vectors along with the desired output labels are used by a Supervised Machine Learning unit 103 of the System to train a model. The Supervised Machine Learning unit 103 finally produces a classifier (e.g., predictor 104) which will be used to predict and answer valid input queries. In an exemplary embodiment, the classifier is a Softmax Classifier.

Unlike a rule-based expert system, the above machine learning based system does not need a routing mechanism that analyzes the fact pattern in the questions and matches the applicable rules until it reaches the conclusion (or fails to reach the conclusion). The above machine learning system is easier to maintain since the rule-based expert system may cause an unexpected effect when an additional rule needs to be added.

The overall NLIDB engine 102 is depicted in FIG. 2. As shown in the figure, the NLIDB engine 102 is composed of two major parts, an NLP Pipeline 201 and a Query Converter 202. The NLP Pipeline 201 extracts entities and relations from the input query. For example, if the input query is "Which patients are diagnosed with {a certain disease}?", then the NLP pipeline 201 extracts 'patient' and 'a certain disease' (which is the name of the disease) as the entities and 'diagnose' as a relation between the two entities from the input query. The NLP Pipeline 201 may also extract auxiliary information that includes aggregation information, data types of the entities (e.g., the certain disease could be of type string), etc. The extracted entities and relations are used to retrieve the actual table and column names stored as metadata of the schema of the database 203. At least one of the table and column names, and the auxiliary information, and the data types are then sent to the Query Converter 202. The Query Converter 202 converts the data received from the NLP pipeline 201 into a database structured query language (SQL) query and uses the SQL query to retrieve query results from the database 203. In an embodiment, the Query Decomposition unit 101 generates input queries of a special type (yes/no questions) and a Query Analysis and Rephrase unit 204 and YES/NO converter 205 are added to the NLIDB system as depicted in FIG. 2 to handle the special types of questions. The Query Analysis and Rephrase unit 204 is introduced to convert the sub-queries into 'How many' type queries and the YES/NO converter 205 is introduced to convert the integer value query results of the 'How many' type queries into binary numbers (either 1 or 0). For example, the Query Analysis and Rephrase unit 204 can convert a yes-no query such as 'did a patient have a certain outcome?' into a how many type query such as 'how many patient had the certain outcome. For example, the YES/NO converter 205 can determine whether the number of patients having the certain outcome is above a threshold that leads to a yes or is not above the threshold to lead to a no. Hence, the NLIDB engine 102 is used to generate feature values (in a binary number) and the set of feature values obtained using a set of sub-queries are used to create a feature vector. A large number of feature vectors can be generated using a large number of clinical records of patients who are diagnosed with a {certain disease}. The Supervised Machine Learning unit 103 uses these feature vectors to train the model and to predict the query answers. The Supervised Machine Learning unit 103 classifies the instances into two or more classes (or labels). The classes are not necessarily mutually exclusive. When the output classes are not mutually exclusive, a multiple number of single class classifiers may be designed.

Due to the complexities and the diversities of the medical and healthcare domain, it is often very challenging to answer the queries with a rule-based (pattern-matching) NLIDB system that applies a set of hard-wired rules to a natural language input query to translate the query to database queries to be answered directly by the underlying database. Hence answering queries in the medical and healthcare domain need help from domain experts so that the system mimics human behavior and reasoning to answer complex queries properly.

An example of healthcare data model is depicted in FIG. 3. The model contains clinical information that includes all the interactions (or encounters) between patients and healthcare providers during a certain time frame in the encounters table 302. The patients table 301 contains information regarding each patient such as personal background and encounter id and history. The clinical determination of disease or disorder for each patient is populated in the diagnosis table 303. The medications prescribed for patients are described in the drug table 304, and an observation table 305 contains all the clinical measurement and laboratory test results. The patient's adverse reaction to drugs is populated in the allergy table 306.

As an example, the system could be asked a query such as "What happens to the patients diagnosed with {a certain disease} and received {a certain medication treatment}?". Although all the information that can be used to infer the correct answer to the query is stored in the database 203, the possible answers to the query such as "Cured", "Not Cured" or "Adverse Event" are not explicitly stored in the database 203. This query cannot be answered without being guided to answer the query using the clinical information stored in the database.

Since the treatment result for each encounter is not stored in the database 203, if a medical expert tries to answer the query and find the trend of the disease and treatment results, he needs to convert the query into the proxies manually as illustrated in FIG. 4 to answer the query. The domain experts should describe their approach to answering such questions in this step and this step requires expert humans to develop and maintain these reasoning rules. For example, the medical expert may answer that a patient is 'Cured' of the disease (e.g., treatment was successful) if he cannot find any follow up encounter of a certain patient who suffered from the same disease in the next certain number of days. He may answer that the patient is 'Not Cured' of the disease (e.g., treatment was not successful) if he sees any subsequent encounter related to the same disease or any medications still being prescribed even after a certain number of days of being diagnosed with the disease. The limitations of the manual process as depicted in FIG. 4 can be mitigated by implementing decision logic developed based on clinical guidelines for a specific disease or a treatment.

Figure 5:
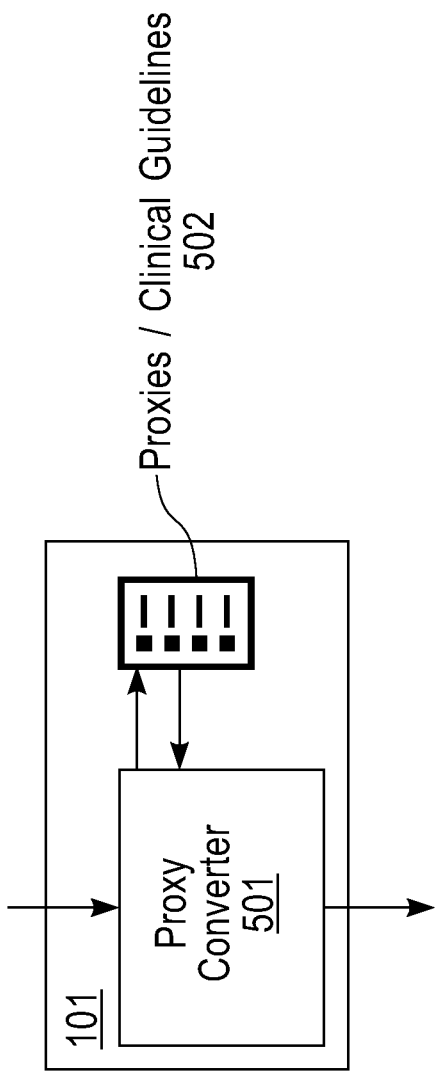
FIG. 5 illustrates a query decomposition example.

As shown in FIG. 5, the Query Decomposition unit 101 converts each proxy used by the domain expert to reason the answer into a sub-query which can be answered by the NLIDB engine 102 with 'yes' or 'no'. When the user query is entered, the Proxy Converter 501 in the Decomposition Unit 101 retrieves proxies (or clinical guidelines) 502 which are manually entered by domain experts offline using the information extracted from the input query such as the name of the disease. Then the Proxy Converter 501 converts the retrieved proxies into a format that can be answered by the NLIDB engine 102. Hence, the set of proxies is converted into a set of simple factoid sub-queries. The sub-queries will be used to extract feature values to train the model. For example, the first proxy "If there are no follow up encounters in the next {certain number of days} then answer "Cured" is converted into a sub-query "Did the patient have any follow up encounters in the next {certain number of days}?". The sub-query is sent to NLIDB engine 102, and the NLIDB engine 102 returns '1' if the answer is 'yes' and returns '0' if the answer is 'no'. The healthcare data source has patient encounter information which includes encounter dates of a patient and the NLIDB engine 102 can answer the sub-query without any complicated reasoning process.

A natural language question is directly mapped to an SQL query and the system returns query results from the database 203. Since the decomposed queries generated by the Query Decomposition unit 101 are yes/no type of questions, the Query Analysis and Rephrase module 204 and the YES/NO Converter 205 are added to the NLIDB engine as illustrated in FIG. 2 to handle the special type of yes/no questions. First, the Query Analysis and Rephrase module 204 analyzes the factoid question and determines whether the sub-query is a yes/no type of question. For the yes/no type of sub-queries, the unit 204 tags the queries with yes/no question tokens and rephrases the queries into 'how many' type of questions. For example, "Did the {patient} have any follow up encounters in the next {certain number of days}?" is rephrased to "How many follow up encounters did {patient} have in the next {certain number of days}?". The NLIDB engine (201 and 202) then returns the number of follow up encounters to the YES/NO converter 205. The NLP pipeline 201 extracts meta data for the entities (patients and encounters) and auxiliary information (date information and aggregation information (e.g., a count)) and sends this information to the Query Convertor 202. The Query Converter 202 converts this information to SQL, retrieves query results (e.g., number of follow up encounters) from the Database Server 203 using the SQL and sends the query results to the YES/NO converter 205. If the token from the Query Analysis and Rephrase module 204 indicates that the original query is a yes/no question, the YES/NO Converter 205 converts the answer into either 1 (Yes) or 0 (No). For example, the YES/NO Converter 205 converts the positive number of follow up encounters to 1 (Yes) and does not change the value if the query result is 0 (No follow up encounter).

The Query Decomposition Unit 101 takes each input query and decomposes it into multiple sub-queries. For example, a sample query "What happens to the patients diagnosed with {a certain disease} and received {a certain medication treatment}?" is decomposed into multiple sub-queries using the proxies described above. The NLIDB engine 102 takes the sub-queries and produces feature vectors by answering the sub-queries using the sample training clinical data. The Learner Unit 100 produces a classifier which maps the input test clinical data to the multiple predicted labels (for example "Cured", "Not Cured" or "Adverse Event"). In this case, the three classes are not mutually exclusive to each other and this is considered a multilabel classification, and an input instance (a patient) can belong to more than one class simultaneously (for example, 'Not Cured' and 'Adverse Event') or to a single class.

In the Supervised Learning performed by the Supervised Machine Learning Unit 103, the supervised example is an input-output pair (x, y) which specifies that y is the desired output for an input feature vector x. For example, in a disease diagnosis system, if the values of x are symptoms, then y should be the names of associated diseases.

FIG. 5 depicts the list of decomposed sub-queries that are converted from the proxies prepared by the domain expert. Hence, the query decomposition unit 101 determines feature representation of the model to be learned. Each decomposed sub-query represents a feature, and it is basically a simple factoid question which is answered with either a 'yes' or a 'no'. The set of simple factoid questions is sent to the NLIDB engine 102 and the NLIDB engine 102 answers the set of questions with '1' if the answer query result from unit 202 into either 1 (Yes) or 0 (No). For example, the YES/NO converter 205 converts the positive number of follow up encounters to 1 (Yes) and does not change the value if the query result is 0 (No follow up encounter).

Figure 6:
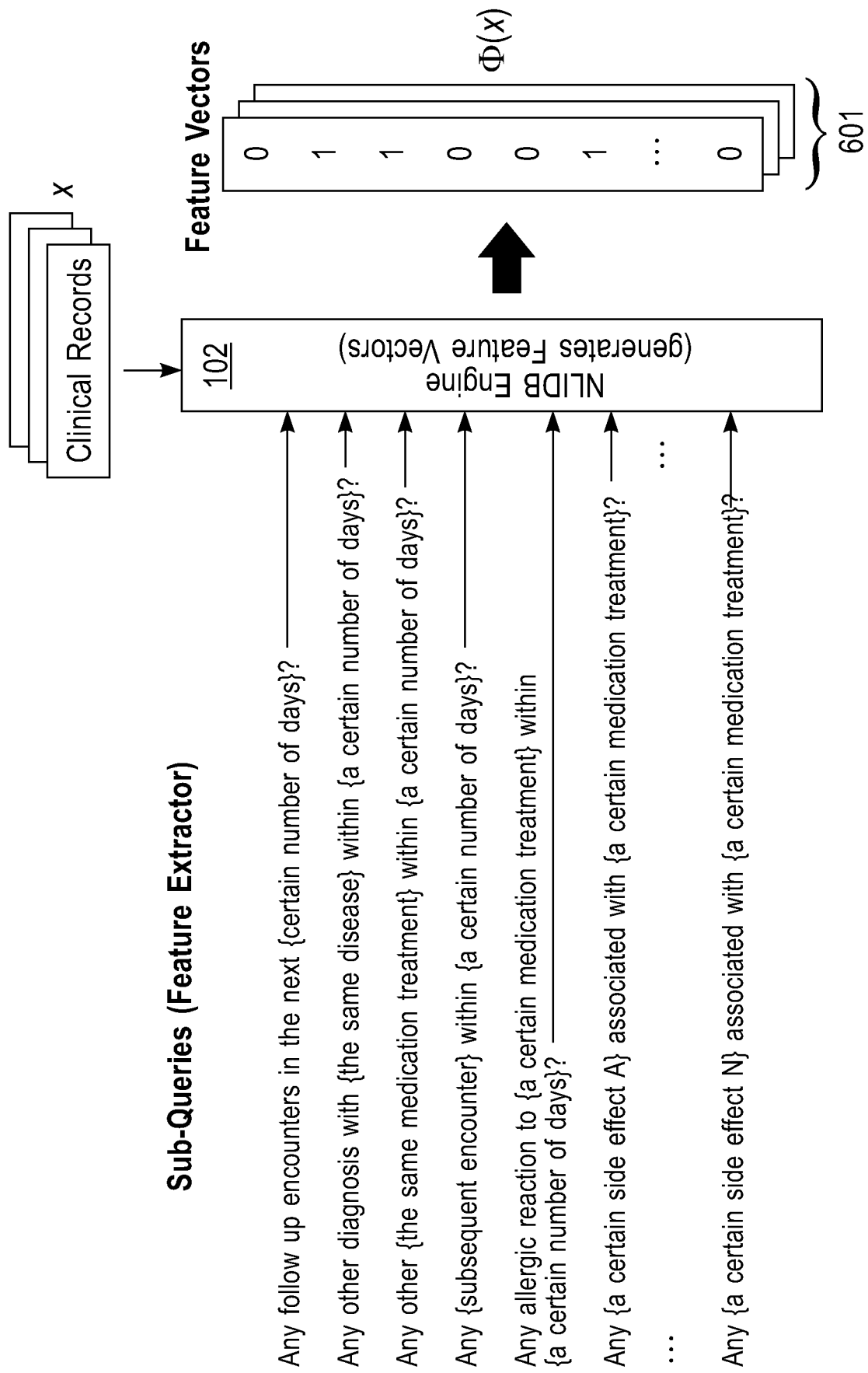
FIG. 6 illustrates a feature extraction process to extract features according to an exemplary embodiment of the inventive concept.

The set of answers to the set of sub-queries are transformed into a feature vector, and hence the question and answering process using NLIDB engine 102 is considered as a feature value extraction process. The details of feature value extraction process are depicted in FIG. 6. During the feature value extraction process, the NLIDB engine 102 generates a feature vector 601 for each training clinical record for each patient who is diagnosed with a certain disease. Hence feature values (in this case integers) are mapped from sub-queries (feature names) and they can be represented as a point in a high dimensional vector space (feature vectors). A multilabel classifier g: X=>Y where X are feature vectors and Y are binary labels is learned. Each feature vector X is labeled as Y=[$y_1$, $y_2$, $y_3$] where $y_1$, $y_2$ and $y_3$ are either 1 or 0 which treats each label as a separate single classification problem. These labels are used as ground truth for the learning process. Learning of classification models in a medicine use case often relies on data labeled by a human expert. The model is trained using the labeled feature vectors. The weight vector (w) shown in FIG. 1 is the parameter of the model that minimizes the error function and specifies the contribution of each feature to the classification (either multiclass classifier or binary classifier depending on the type of input query). Since multiple labels (or classes) exist in the example as output, a weight matrix is constructed using multiple weight vectors [$w_1$, $w_2$, $w_3$] where each $w_1$, $w_2$ and $w_3$ is weight vector corresponding to each label ('Cured', 'Not Cured' and 'Adverse Event').

Figure 7:
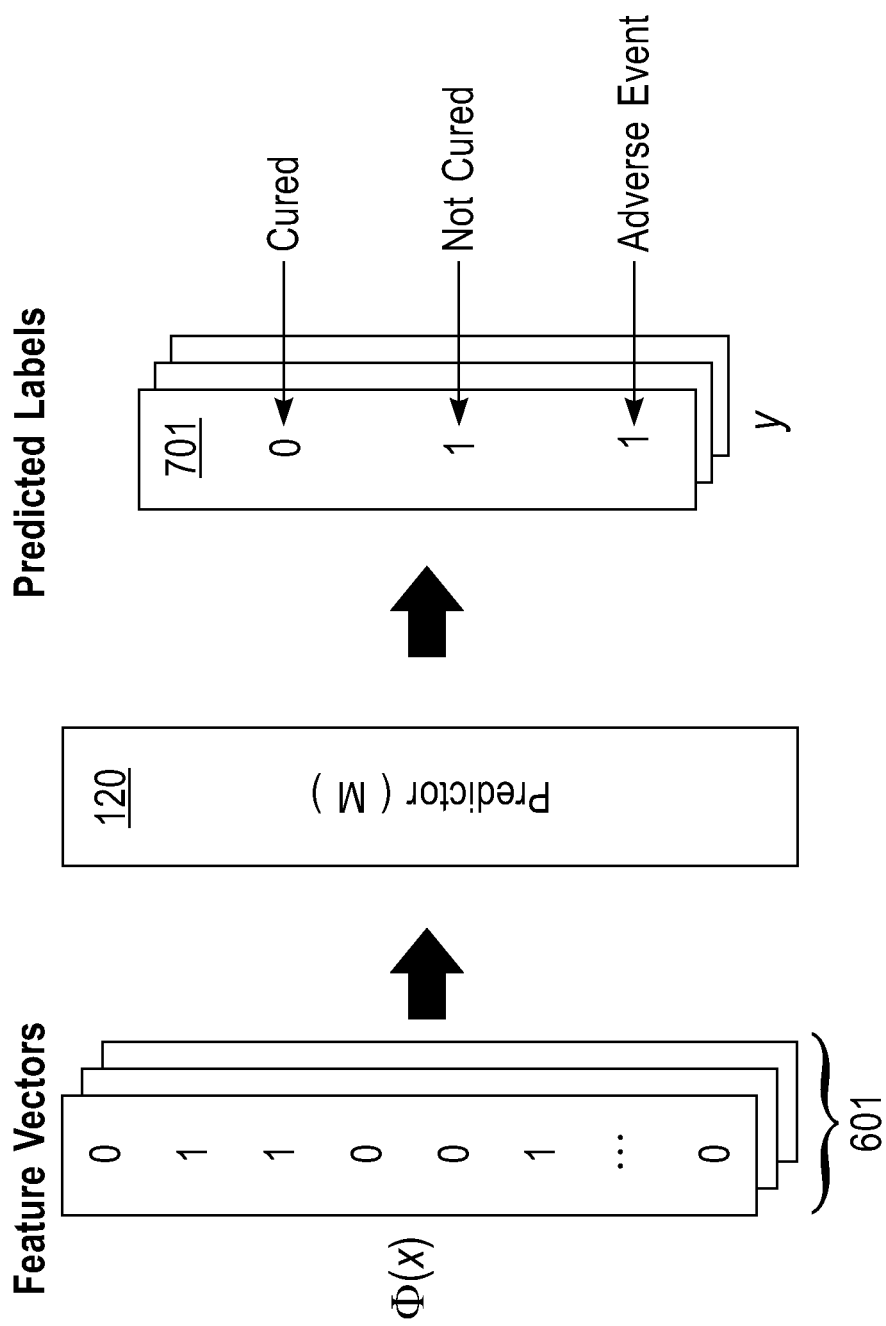
FIG. 7 illustrates exemplary labels that may be output by a predictor of the system based on the extracted feature vectors.

When the training of the model is done using training clinical records, the feature vector that is extracted with the test clinical data and the weight vector that is generated in the training process are used to calculate the weighted combination of features that represent the degree of confidence. In an embodiment, the Softmax classification technique is used to compute the normalized probability (or confidence score) for each class label, and the confidence score is used to identify the most likely output labels among multiple possible output classes to the input query. While an embodiment focuses on a multiclass classification problem where the output classes are mutually exclusive to each other, it is also possible that the output labels are not mutually exclusive as in the example shown in FIG. 7 and a patient belongs to 'Not Cured' as well as 'Adverse Event' classes simultaneously as 701. This case represents a different classification task and this classification problem can be broken into a multiple single class classification problem and a classifier is built for each class where the training data consists of the set of patients in the class (positive labels) and its complement. After the training, given the test patient data, each classifier is applied separately and the decision of one classifier has no influence on the decision of the other classifiers.

Figure 8:
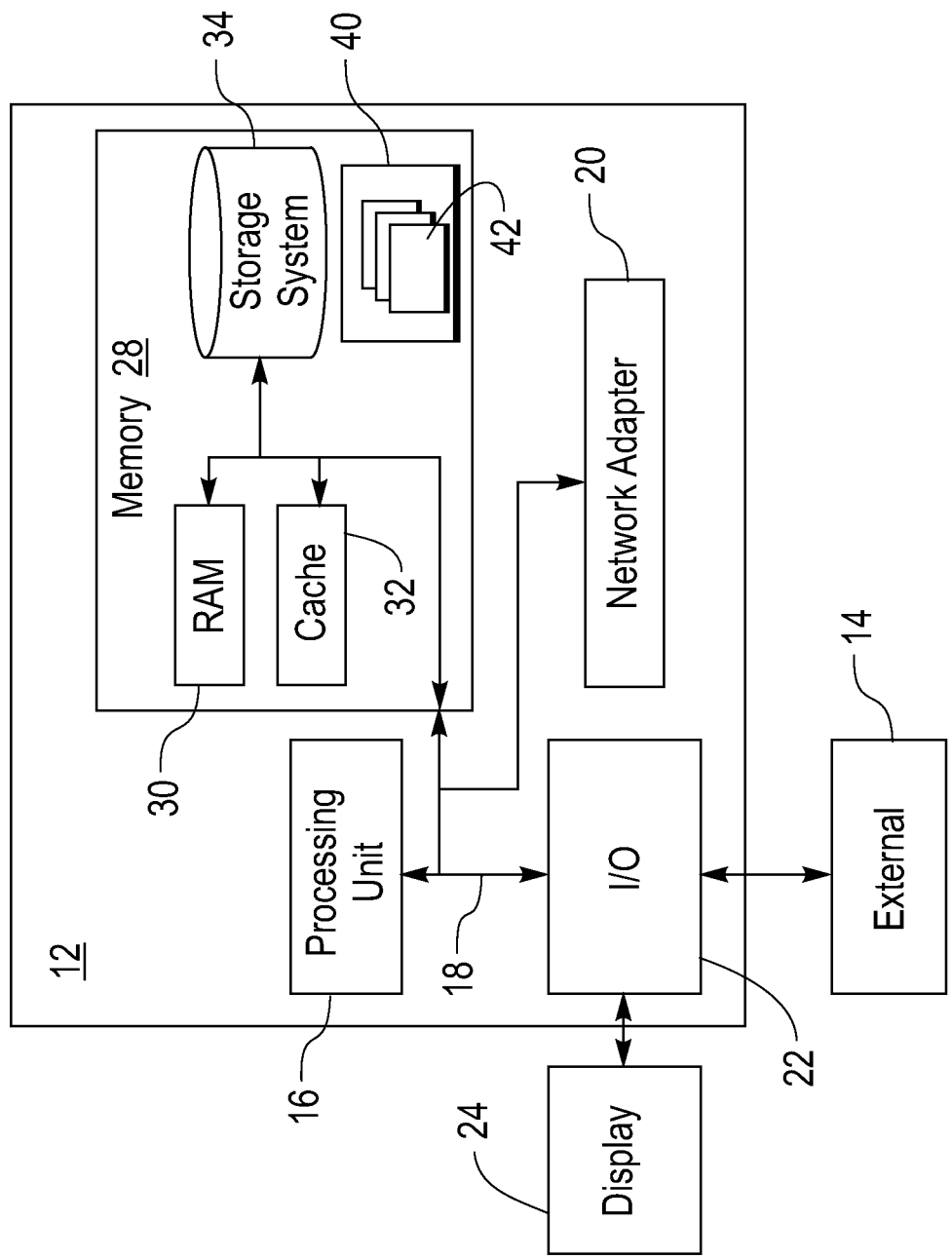
FIG. 8 illustrates a computer that may be used to implement the system.

FIG. 8 illustrates a computer including a processor that may be used to execute a computer program that implements one or more elements of the system of FIG. 1. The computer is shown in the form of a general-purpose computing device. The components of the computer 12 may include, but are not limited to, one or more processors or processing units 16, a system memory 28, and a bus 18 that couples various system components including system memory 28 to processor 16. The system memory 28 may store one or more of the above described clients for execution by the processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnect (PCI) bus.

The computer may include a variety of computer system readable media. Such media may be any available media that is accessible by the computer 12, and it includes both volatile and non-volatile media, removable and non-removable media.

The system memory 28 can include computer system readable media in the form of volatile memory, such as random access memory (RAM) 30 and/or cache memory 32. The memory 28 may store the database 203 shown in FIG. 2 or the tables shown in FIG. 3. The computer may further include other removable/non-removable, volatile/non-volatile computer system storage media. By way of example, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

A program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. The program modules 42 generally carry out the functions and/or methodologies of embodiments of the invention as described herein.

The computer 12 may also communicate with one or more external devices 14 such as a keyboard, a pointing device, a display 24, etc.; one or more devices that enable a user to interact with the computer 12; and/or any devices (e.g., network card, modem, etc.) that enable the computer 12 to communicate with one or more other computing devices. Such communication can occur via Input/Output (I/O) interfaces 22. The computer 12 can communicate with one or more networks such as a local area network (LAN), a general wide area network (WAN), and/or a public network (e.g., the Internet) via a network adapter 20. As depicted, the network adapter 20 communicates with the other components of computer 12 via the bus 18. It should be understood that although not shown, other hardware and/or software components could be used in conjunction with the computer 12. Examples of these other hardware and/or software components include, but are not limited to: microcode, device drivers, redundant processing units, external disk drive arrays, RAID systems, tape drives, and data archival storage systems.

In an exemplary embodiment, the computer 12 includes a microphone so that a user can speak the input query, and software and/or hardware to convert the spoken query into a textual input query that can be passed to the Query Decomposition Unit 100.

In an exemplary embodiment, one or more portions of the system of FIG. 1 are provided in a medical device (e.g., a band, a patch) worn by a user to create a personal intelligent assistant device.

Figure 9:
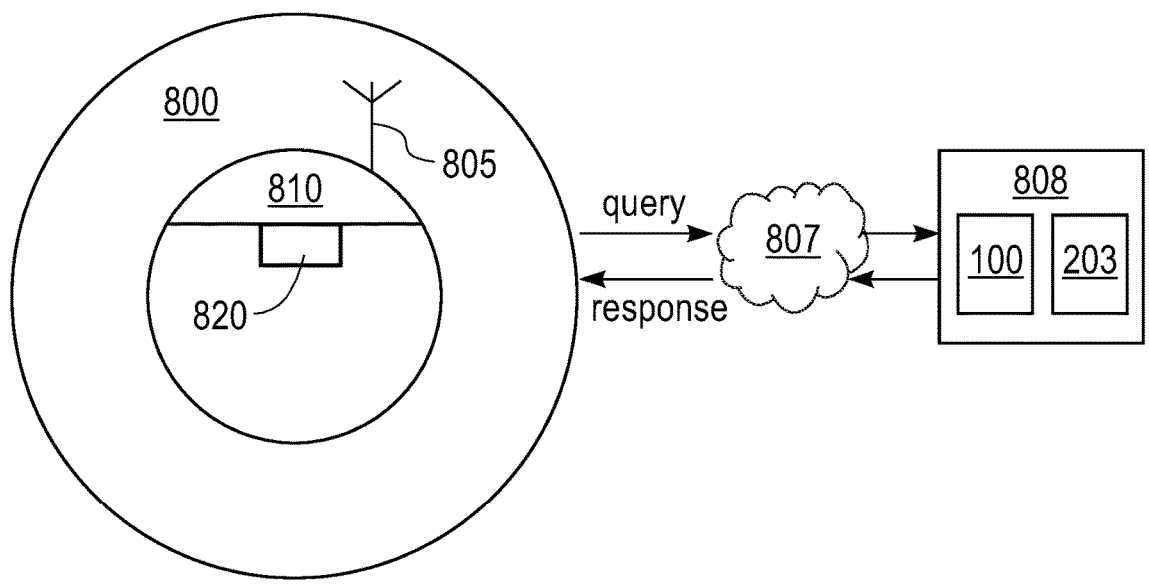
FIG. 9 illustrates a medical band according to an exemplary embodiment of the inventive concept.

FIG. 9 illustrates a band 800 including a housing 810 and optionally at least one medical sensor 820. The housing 810 may communicate a query of a user of the band 800 to a remote server 808 across a computer network 807 (e.g., the Internet) using an antenna 805. The remote server 808 includes the Learner Unit 100.

Figure 10:
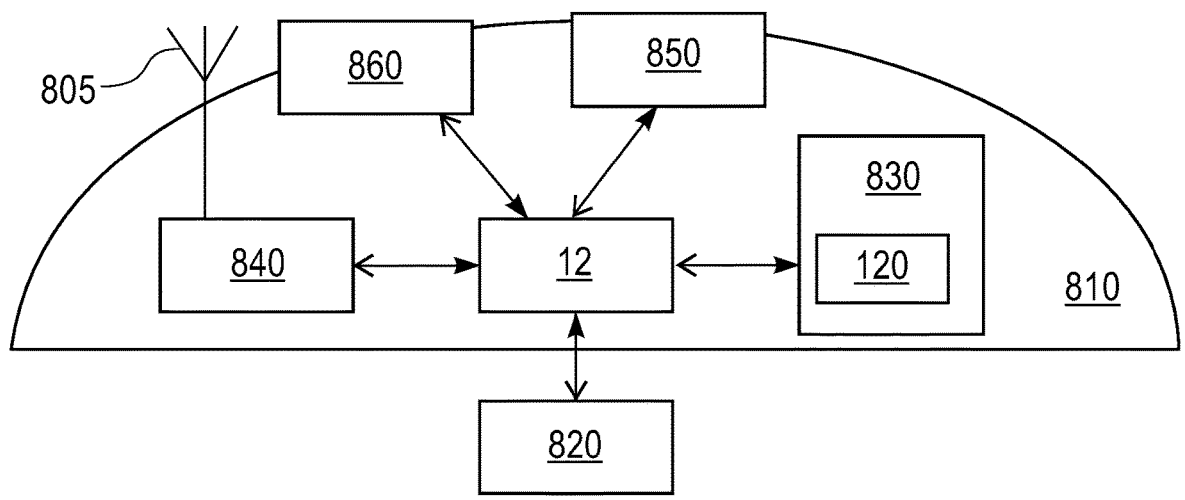
FIG. 10 illustrates a portion of the medical band according to an exemplary embodiment of the inventive concept.

FIG. 10 illustrates the housing 810 according to an exemplary embodiment of the inventive concept. The housing includes a processor 12 or a device interface, a memory 830 storing the Predictor Unit 120, a transceiver 840, a microphone 850, and a speaker 860. The processor 12 may execute the Predictor Unit 120, control the medical sensor 820, control the microphone 850, control the speaker 860, and use the transceiver 840 to transmit one or more queries to the remote server 808.

The memory 830 may store personal information about the user (e.g., age, weight, gender, etc) that wears the band 800. The band 800 may additionally include a port (e.g., USB port) that enables the band 800 to be interfaced with a computer to load the personal information or update the Predictor Unit 120. The band 800 additionally includes a power supply (not shown) such as a rechargeable battery to power the illustrated components. The battery may be charged by connecting the port to a computer or to an external power supply.

The user can speak a query that is captured by the microphone. A NDLIB engine (e.g., 102) of the Predictor Unit 120 within the band 800 can convert the captured speech to a textual query, convert the textual query to a plurality of sub-queries, convert the sub-queries into structured query language (SQL) queries, remotely apply the SQL queries across a computer network 807 to a database 203 using the transceiver 840 to generate responses, generate features from the responses, and output the features to a classifier unit 104 of the Predictor Unit 120. The classifier unit 104 performs a classification algorithm on the features to identify one a plurality of classes (e.g., cured, not cured, etc.).

The NLDIB engine can augment the entered query with data captured by the medical sensor 820. For example, the user can speak a query such as, "Am I healthy" or "Am I well", and NLIDB engine (e.g., 102) can augment the query to include sensor data sensed by the medical sensor 820 and the personal information, convert the augmented query into a plurality of sub-queries, convert the sub-queries into SQL queries, and remotely apply the SQL queries across the computer network 807 to the database 203 using the transceiver 840 to generate responses, generate features from the responses, and output the features to a classifier unit 104 of the Predictor Unit 120. The classifier unit 104 performs a classification algorithm on the features to identify one a plurality of classes (e.g., well, not well, etc.).

The sensor data may include an oxygen saturation percentage, a pulse, a body temperature, blood pressure readings (systolic and/or diastolic), blood glucose levels, etc. For example, if the sensor data includes a pulse of 180, a glucose level of 70 mg/dl and personal information of age 40 and gender male, the device could augment the input Query of "Am I healthy" to "Is it OK for a man of 40 to have a pulse of 180 and a glucose level of 70 mg/dl". For example, the Learner Unit 100 could have been trained with similar input queries to create a Predictor 104 that can generate a label that answers the augmented input query. For example, the label can indicate that the user is OK, is not OK, or should seek medical attention. For example, if the Predictor 104 indicates the user is OK, the medical device could use the speaker 860 to output speech indicating the user is OK. For example, if the Predictor 104 indicates the user is not OK or needs to seek medical attention, the medical device could use the speaker to output speech indicating the user is not OK or needs to seek medical attention. The medical device could also include a light (e.g., an LED) that displays a certain color to indicate a response to the query (e.g., green for OK/well and red for not OK/not well).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A system for responding to natural language medical queries, the system comprising:
    a memory storing a computer program;
    a processor configured to execute the computer program, wherein the computer program automatically decomposes an input medical related user query comprising a natural language question for a given disease into medical related sub-queries using pre-defined clinical guidelines for the disease, rephrases the sub-queries into yes-no queries answerable with a yes or a no, extracts feature values from the yes-no queries and a relational database storing clinical records, generates a feature vector from the extracted feature values, and applies the feature vector along with desired output labels to a supervised machine learning algorithm to generate a classifier configured to answer a new medical related user query.

2. The system of claim 1, wherein the computer program decomposes the input medical related user query by:
    extracting entities and relationships between the entities and data types of the entities from the input medical related user query; and
    retrieving table and column names stored as metadata of schema of the database, from the extracted entities and relationship.

3. The system of claim 2, wherein the entities include patients and the given disease, and the relationships include the patients diagnosed with the given disease.

4. The system of claim 2, wherein the computer program extracts the feature values by:
    generating database structure query language (SQL) queries from the table and column names and the data types;
    applying the SQL queries to the database to generate query results; and
    generating the feature values from the query results.

5. The system of claim 1, wherein each yes-no query indicates whether a patient had a certain medical history regarding the given disease.

6. The system of claim 5, wherein the computer program extracts the feature values by:
    converting the yes-no query into a how-many query that indicates how many times the patient had the certain medical history;
    applying the how-many query to the database to return an integer value;
    converting the integer value into a binary number; and
    generating the feature values from the binary number.

7. The system of claim 1, wherein the output labels include labels indicating one of 'Cured', 'Not Cured, and 'Adverse Event'.

8. The system of claim 7, wherein the classifier uses a Softmax classification technique to compute a confidence score for each of the labels to identify which of the labels to apply to the new medical related user query.

9. The system of claim 8, further comprising:
    extracting entities and relationships between the entities and data types of the entities from the new medical related user query;
    retrieving table and column names stored as metadata of schema of the database, from the extracted entities and relationships;
    generating database structure query language (SQL) queries from the table and column names and the data types; applying the SQL queries to the database to generate query results;
    generating a new feature vector from the query results; and
    applying the new feature vector to the classifier to identify one of the output labels.

10. A method for responding to natural language medical queries, comprising:
    automatically decomposing an input medical related user query comprising a natural language question for a given disease into medical related sub-queries using pre-defined clinical guidelines for the disease;
    rephrasing the sub-queries into yes-no queries answerable with a yes or a no;
    extracting feature values from the yes-no queries and a relational database storing clinical records;
    generating a feature vector from the extracted feature values;
    applying the feature vector along with desired output labels to a supervised machine learning algorithm to generate a classifier; and
    applying a new medical related user query to the classifier.

11. The method of claim 10, wherein the decomposing comprises:
    extracting entities and relationships between the entities and data types of the entities from the input medical related user query; and
    retrieving table and column names stored as metadata of schema of the database, from the extracted entities and relationship.

12. The method of claim 11, wherein the entities include patients and the given disease, and the relationships include the patients diagnosed with the given disease.

13. The method of claim 11, wherein the extracting comprises:
    generating database structure query language (SQL) queries from the table and column names and the data types;
    applying the SQL queries to the database to generate query results; and
    generating the feature values from the query results.

14. The method of claim 10, each yes-no query indicates whether a patient had a certain medical history regarding the given disease.

15. The method of claim 14, wherein the extracting comprises:
    converting the yes-no query into a how-many query that indicates how many times the patient had the certain medical history;
    applying the how-many query to the database to return an integer value; converting the integer value into a binary number; and
    generating the feature values from the binary number.

16. The method of claim 10, wherein the output labels include labels indicating one of 'Cured', 'Not Cured, and 'Adverse Event'.

17. The method of claim 16, wherein the classifier uses a Softmax classification technique to compute a confidence score for each of the labels to identify which of the labels to apply to the new medical related user query.

18. The method of claim 17, wherein the applying of the new medical related user query comprises:
    extracting entities and relationships between the entities and data types of the entities from the new medical related user query;
    retrieving table and column names stored as metadata of schema of the database, from the extracted entities and relationships;
    generating database structure query language (SQL) queries from the table and column names and the data types;
    applying the SQL queries to the database to generate query results; generating a new feature vector from the query results; and
    applying the new feature vector to the classifier to identify one of the output labels.

19. A computer program product for responding to natural language medical queries, the computer program product comprising a computer readable storage medium having program code embodied therewith, the program code executable by a processor, to perform method steps comprising instructions for:
    automatically decomposing an input medical related user query comprising a natural language question for a given disease into medical related sub-queries using pre-defined clinical guidelines for the disease;
    rephrasing the sub-queries into yes-no queries answerable with a yes or a no;
    extracting feature values from the yes-no queries and a relational database storing clinical records;
    generating a feature vector from the extracted feature values;
    applying the feature vector along with desired output labels to a supervised machine learning algorithm to generate a classifier; and
    applying a new medical related user query to the classifier.

20. The computer program product of claim 19, wherein the applying of the new medical related user query comprises:
    extracting entities and relationships between the entities and data types of the entities from the new medical related user query;
    retrieving table and column names stored as metadata of schema of the database, from the extracted entities and relationships;
    generating database structure query language (SQL) queries from the table and column names and the data types;
    applying the SQL queries to the database to generate query results; generating a new feature vector from the query results; and
    applying the new feature vector to the classifier to identify one of the output labels.

* * * * *